(12) United States Patent
Torrens Jover et al.

(10) Patent No.: US 7,345,057 B2
(45) Date of Patent: Mar. 18, 2008

(54) 5-HT7 RECEPTOR ANTAGONISTS

(75) Inventors: Antoni Torrens Jover, Barcelona (ES); Susana Yenes Minguez, Barcelona (ES); Jose Mas Prio, Barcelona (ES); Luz Romero Alonso, Barcelona (ES); Alberto Dordal Zueras, Barcelona (ES); Helmut H. Buschmann, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 485 days.

(21) Appl. No.: 11/048,992

(22) Filed: Feb. 2, 2005

(65) Prior Publication Data

US 2006/0142332 A1  Jun. 29, 2006

(30) Foreign Application Priority Data

Dec. 28, 2004  (EP) ................................. 04380279

(51) Int. Cl.
*C07D 401/02*  (2006.01)
*A61K 31/4709*  (2006.01)

(52) U.S. Cl. ...................... 514/307; 546/148
(58) Field of Classification Search ................ 546/148; 514/307
See application file for complete search history.

(56) References Cited

FOREIGN PATENT DOCUMENTS

| EP | 0 021 580 | 12/1983 |
|---|---|---|
| EP | 0 076 072 | 5/1987 |
| WO | WO 97/29097 | 8/1997 |
| WO | WO 97/48681 | 12/1997 |
| WO | WO 97/49695 | 12/1997 |
| WO | WO 99/24022 | 5/1999 |
| WO | WO 00/00472 | 1/2000 |
| WO | WO 03/048118 | 6/2003 |

OTHER PUBLICATIONS

Terron, J. A., IDrugs, vol. 1(3), pp. 302-301, 1998.
Lovenberg et al., Neuron, vol. 11, pp. 449-458, 1993.
Terron, J. A., Br. J. Pharmacol., vol. 121, pp. 563-571, 1997.
Schoefter et al., Br. J. Pharmacol., vol. 117, pp. 993-994, 1996.
Terron, J. A., Eur. J. Pharmacol., vol. 439, pp. 1-11, 2002.
De Ponti et al., Drugs, vol. 61, pp. 317-332, 2001.
Read et al., Br. J. Pharmacol., vol. 140, pp. 53-60, Jul. 29, 2003.
Wesolowska, A., Polish J. Pharmacol., vol. 54, pp. 327-341, 2002.
Whaley, Organic Reactions, vol. 6 (chapter 3), pp. 151-190, 1951.
Munson et al., Anal. Biochem., vol. 107, pp. 220-239, 1980.
Vermeulen et al., J. Med. Chem., vol. 47, pp. 5451-5466, Sep. 23, 2004.
European Patent Office, European Search Report for EP 04380279.2, issued May 23, 2005.

*Primary Examiner*—Zinna N. Davis
(74) *Attorney, Agent, or Firm*—Morgan & Finnegan, L.L.P.

(57) ABSTRACT

The invention relates to compounds having pharmacological activity towards the 5-HT7 receptor, and more particularly to some some tetrahydroisoquinoline substituted sulfonamide compounds, to processes of preparation of such compounds, to pharmaceutical compositions comprising them, and to their use for the treatment and or prophylaxis of a disease in which 5-HT is involved, such as CNS disorders.

31 Claims, No Drawings

5-HT7 RECEPTOR ANTAGONISTS

FIELD OF THE INVENTION

The present invention relates to compounds having pharmacological activity towards the 5-HT7 receptor, and more particularly to some tetrahydroisoquinoline substituted sulfonamide compounds, to processes of preparation of such compounds, to pharmaceutical compositions comprising them, and to their use in therapy, in particular for the treatment and or prophylaxis of a disease in which 5-HT$_7$ is involved, such as CNS disorders.

BACKGROUND OF THE INVENTION

The search for new therapeutic agents has been greatly aided in recent years by better understanding of the structure of proteins and other biomolecules associated with target diseases. One important class of proteins that has been the subject of extensive study is the family of 5-hydroxytryptamine (serotonin, 5-HT) receptors. The 5-HT$_7$ receptor discovered in 1993 belongs to this family and has attracted great interest as a valuable new drug target (Terrón, J. A. *Idrugs*, 1998, vol. 1, no. 3, pages 302-310:"The 5HT$_7$ receptor: A target for novel therapeutic avenues?").

5-HT$_7$ receptors have been cloned from rat, mouse, guinea pig and human cDNA and exhibit a high degree of interspecies homology (approx. 95%), but it is unique in that it has a low sequence homology with other 5-HT receptors (less than 40%). Its expression pattern, in particular structures of the central nervous system (CNS) (highest in hypothalamus (in particular suprachiasmatic nuclei) and thalamus) and other peripheral tissues (spleen, kidney, intestinal, heart and coronary arthery), implicates the 5-HT$_7$ receptor in a variety of functions and pathologies. This idea is reinforced by the fact that several therapeutic agents, such as tricyclic antidepressants, typical and atypical antipsychotics and some 5-HT$_2$ receptor antagonists, display moderate to high affinity for both recombinant and functional 5-HT$_7$ receptors.

Functionally, the 5-HT$_7$ receptor has been implicated in regulation of circadian rhythms in mammals (Lovenberg, T. W. et al. *Neuron*, 1993, 11:449-458 *"A novel adenylyl cyclase-activating serotonin receptor (5-HT$_7$) implicated in the regulation of circadian rhythms"*). It is known that disruption of circadian rhythms is related to a number of CNS disorders including depression, seasonal affective disorder, sleep disorders, shift worker syndrome and jet lag among others.

Distribution and early pharmacological data also suggest that the 5-HT$_7$ receptor is involved in the vasodilatation of blood vessels. This has been demonstrated in vivo (Terrón, J. A., *Br J Pharmacol*, 1997, 121:563-571 *"Role of 5-HT$_7$ receptors in the long lasting hypotensive response induced by 5-hydroxytryptamine in the rat"*). Thus selective 5-HT$_7$ receptor agonists have a potential as novel hypertensive agents.

The 5-HT$_7$ receptor has also been related with the pathophysiology of migraine through smooth muscle relaxation of cerebral vessels (Schoeffter, P. et al., 1996, *Br J Pharmacol*, 117:993-994; Terrón, J. A., 2002, *Eur. J. Pharmacol.*, 439: 1-11 *"Is the 5-HT$_7$ receptor involved in the pathogenesis and prophylactic treatment of migraine?"*). In a similar manner, involvement of 5-HT$_7$ in intestinal and colon tissue smooth muscle relaxation makes this receptor a target for the treatment of irritable bowel syndrome (De Ponti, F. et al., 2001, *Drugs*, 61:317-332 *"Irritable bowel syndrome. New agents targeting serotonin receptor subtypes"*). Recently, it has also been related to urinary incontinence (*British J of Pharmacology*, Sep. 2003, 140(1) 53-60: "Evidence for the involvement of central 5HT-7 receptors in the micurition reflex in anaesthetized female rats").

In view of the potential therapeutic applications of agonists or antagonists of the 5HT$_7$ receptor, a great effort has been directed to find selective ligands. Despite intense research efforts in this area, very few compounds with selective 5-HT$_7$ antagonist activity have been reported (Wesolowska, A., *Polish J. Pharmacol.*, 2002, 54: 327-341, *"In the search for selective ligands of 5-HT$_5$, 5-HT$_6$ and 5-HT$_7$ serotonin receptors"*).

WO 97/48681 discloses sulfonamide derivatives, which are 5-HT$_7$ receptor antagonists, for the treatment of CNS disorders. The sulphur atom is linked to an aromatic group and to a N-containing heterocyclic group, optionally containing a further heteroatom selected from oxygen or sulphur.

WO 97/29097 describes sulfonamide derivatives for the treatment of disorders in which antagonism of the 5-HT$_7$ receptor is beneficial. The sulphur atom is linked to an aromatic group and to a $C_1$-$C_6$ alkyl substituted N atom.

WO97/49695 describes further sulfonamide derivatives in which the N linked to the sulphur atom is also fully substituted, for example forming part of a piperidine.

WO 03/048118 describes another group of 5HT$_7$ receptor antagonists. In this case aryl and heteroaryl sulfonamide derivatives wherein the sulfonamide group is a substituent on a cycloalkane or cycloalkene ring which additionally bears an amino susbtituent. The N linked to sulphur atom is fully substituted.

WO99/24022 discloses tetrahydroisoquinoline derivatives for use against CNS disorders and binding to serotonin receptors, in particular 5-HT$_7$.

WO 00/00472 refers to compounds which are 5-HT7 receptor antagonists. The compounds contain a N-containing fused heterocycle such as tetrahydroisoquinoline.

EP 21580 and EP 76072 describe sulfonamide compounds having antiarrhythmic activity, corresponding to the formula $R_2N(CH_2)_n$—NH—$SO_2R_1$, 5-HT$_7$ activity is not mentioned.

There is still a need to find compounds that have pharmacological activity towards the receptor 5-HT$_7$, being both effective and selective, and having good "drugability" properties, i.e. good pharmaceutical properties related to administration, distribution, metabolism and excretion.

SUMMARY OF THE INVENTION

We have now found a family of structurally distinct class of sulfonamide compounds which are particularly selective inhibitors of the 5-HT$_7$ receptor. The compounds present a tetrahydroisoquinoline moiety, linked through a 3, or 4-methylene piperidine with a sulfonamide moiety. We have found that the compounds display IC-50 values in the nM range (10-100 nM) at human 5-HT7 receptors and exhibit selectivity for these receptors vs 5-HT1A, 5-HT2A, 5-HT2B, 5-HT2C, 5-HT3, 5-HT4, 5-HT5A, D1, D2, D3, D4, adrenergic α1A, α1B, α1B, β1, and β2 receptors.

In one aspect the invention is directed to a compound of the formula I:

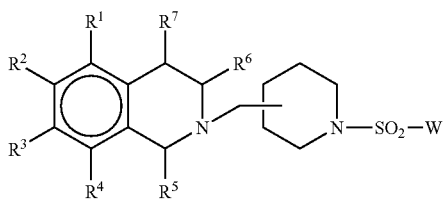

wherein

W is a substituted or unsubstituted alkyl, substituted or unsubstituted alkenyl, substituted or unsubstituted cycloalkyl, substituted or unsubstituted aryl, substituted or unsubstituted heterocyclyl;

$R^1$, $R^2$, $R^3$, $R^4$, $R^5$, $R^6$ and $R^7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR^8$, —$C(O)OR^8$, —$C(O)NR^8R^9$, —HC=$NR^8$, —CN, —$OR^8$, —$OC(O)R^8$, —$S(O)_t$—$R^8$, —$NR^8R^9$, —$NR^8C(O)R^9$, —$NO^2$, —N=$CR^8R^9$ or halogen; wherein t is 1, 2 or 3;

$R^8$ and $R^9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;

and wherein the 1,2,3,4-tetrahydroisoquinoline group is linked through metilene to positions 3 or 4 of the piperidine ring;

or a pharmaceutically acceptable salt, isomer, prodrug or solvate thereof.

In another aspect the invention is directed to a pharmaceutical composition which comprises a compound as above defined or a pharmaceutically acceptable salt, enantiomer, prodrug or solvate thereof, and a pharmaceutically acceptable carrier, adjuvant or vehicle.

In a further aspect the invention is directed to the use of a compound as defined above in the manufacture of a medicament for the treatment of a 5-$HT_7$ mediated disease or condition, i.e. diseases caused by failures in central and peripheral serotonin-controlling functions, such as pain, sleep disorder, shift worker syndrome, jet lag, depression, seasonal affective disorder, migraine, anxiethy, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

DETAILED DESCRIPTION OF THE INVENTION

The typical compounds of this invention effectively and selectively inhibit the 5-HT7 receptor vs. other 5-HT receptors such as 5-HT1A, 5-HT2A, 5-HT2B, 5-HT2C, 5-HT3, 5-HT4,5-HT5A, D1, D2, D3, D4, adrenergic α1A, α1B, α1B, β1, Tachykinin NK-1 opiate, GABA, estrogen, glutamate, adenosine, nicotinic, muscarinic receptors and calcium, potassium and sodium channels and neurotransmitter transporters (serotonin, dopamine, norepinephrine, GABA).

In the above definition of compounds of formula (I) the following terms have the meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2 C atoms and having one or more unsaturated bonds.

"Cycloalkyl" refers to a stable 3-to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

"Heterocyclyl" refers to a stable 3-to 15 membered ring radical which consists of carbon atoms and from one to five heteroatoms selected from the group consisting of nitrogen, oxygen, and sulfur, preferably a 4-to 8-membered ring with one or more heteroatoms, more preferably a 5-or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e.g., methoxy, ethoxy, propoxy, etc.

"Alkoxycarbonyl" refers to a radical of the formula-C(O) ORa where Ra is an alkyl radical as defined above, e.g., methoxycarbonyl, ethoxycarbonyl, propoxycarbonyl, etc.

"Alkylthio" refers to a radical of the formula-SRa where Ra is an alkyl radical as defined above, e.g., methylthio, ethylthio, propylthio, etc.

"Amino" refers to a radical of the formula-NH2, —NHRa or —NRaRb, optionally quaternized.

"Halo" or "hal" refers to bromo, chloro, iodo or fluoro.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Particular individual compounds of the invention include the compounds 1-78 in the examples, either as salts or as free bases.

In an embodiment the tetrahydroisoquinoline in the compounds of formula I above is not substituted, $R^1$ to $R^7$ are all H. Good activity results are obtained with such compounds.

In another embodiment $R^2$ is alkoxy, preferably methoxy and the rest of the substitutents of the tetrahydroisoquinoline ($R^1$ and $R^3$ to $R^7$) are H.

In another embodiment $R^2$ and $R^3$ are alkoxy, preferably methoxy and the rest of the substitutents of the tetrahydroisoquinoline ($R^1$ and $R^4$ to $R^7$) are H.

In another embodiment the group W linked to the sulfonamide is aromatic, such as substituted or unsubstituted aryl, substituted or unsubstituted heterocyclyl, preferably substituted or unsubstituted phenyl. Good results were obtained when W is alkyl, alkoxy and/or halo substituted phenyl. In particular halo substituted phenyl, having one or more halo substituents being the same or different are preferred.

In an embodiment it is important that 1,2,3,4-tetrahydroisoquinoline group is linked through metilene to position 4 of the piperidine ring. Best results were obtained with this position linking the tetrahydroisoquinoline.

The above embodiments and preferences for W, $R^1$ to $R^7$ and the position of linkage can be combined to give further preferred compounds.

Representative compounds of the above embodiments which are preferred are: 2-[1-(5-Chloro-2,4-difluoro-benzene sulfonyl)-piperidin-4-ylmethyl]-1,2,3,4-tetrahydroisoquinoline hydrochloride, 2-[1-(2-Chloro-benzenesulfonyl)-piperidin-4-ylmethyl]-1,2,3,4-tetrahydro-isoquinoline hydrochloride, 2-[1-(2,5-Dichloro-benzenesulfonyl)-piperidin-4-ylmethyl]-1,2,3,4-tetrahydro-isoquinoline hydrochloride, 2-[1-(Toluene-3-sulfonyl)-piperidin-4-ylmethyl]-1,2,3,4-tetrahydroisoquinoline hydrochloride, 2-[1-(2-Chloro-4,5-difluoro-benzenesulfonyl)-piperidin-4-ylmethyl]-1,2,3,4-tetrahydroisoquinoline hydrochloride, 2-[1-(4-Chloro-2,5-dimethyl-benzenesulfonyl)-piperidin-4-ylmethyl]-1,2,3,4-tetrahydroisoquinoline hydrochloride, 2-[1-(2-Bromo-benzenesulfonyl)-piperidin-4-ylmethyl]-1,2,3,4-tetrahydro-isoquinoline hydrochloride, 2-[1-(Naphtalene-1-sulfonyl)-piperidin-4-ylmethyl]-1,2,3,4-tetrahydroisoquinoline hydrochloride.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

Unless otherwise stated, the compounds of the invention are also meant to include compounds which differ only in the presence of one or more isotopically enriched atoms.

For example, compounds having the present structures except for the replacement of a hydrogen by a deuterium or tritium, or the replacement of a carbon by a $^{13}$C- or $^{14}$C-enriched carbon or $^{15}$N-enriched nitrogen are within the scope of this invention.

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glucamine and basic aminoacids salts.

Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of formula (I) defined above can be obtained by available synthetic procedures.

Compounds of Formula (Ia) or (Ib) can be prepared by the coupling of compounds of Formula (IIa) or (IIb):

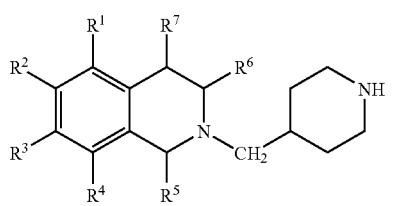
(IIa)

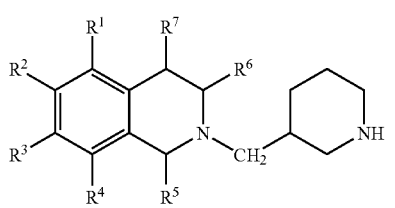
(IIb)

in which $R^1$-$R^7$ are as defined in Formula (I), with a compound of Formula (III):

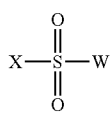
(III)

in which W is as defined in Formula (I) and X is an halogen, typically Cl.

The reaction of compounds of formulas (II) and (III) is preferably carried out in an aprotic solvent, but not limited to, such as dichloromethane in the presence of an organic base, such as diisopropylethylamine or triethylamine.

Compounds of Formula (III) are commercially available or can be prepared by conventional methods.

Compounds of Formula (II) can be commercially available or prepared from compounds of Formula (IV). Compounds of Formula (IV) can also be commercially available or synthesized by conventional methods, such as Pictet-Spengler reaction from substituted phenylethyl amines and ketones or aldehydes substituted with $R^5$, as shown in Scheme 1.

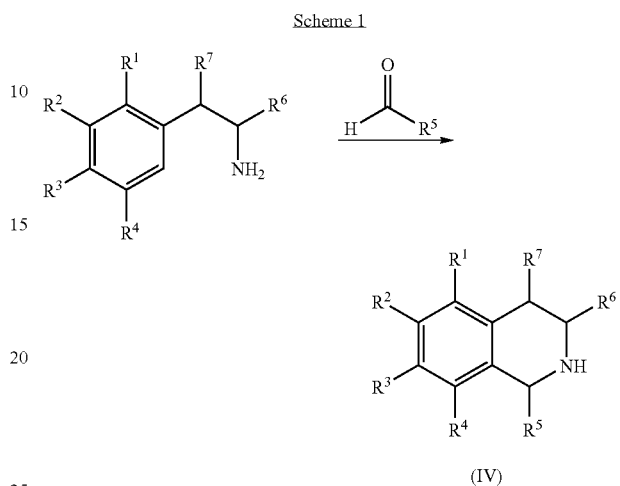

Scheme 1

(IV)

Compounds of Formula (II) can be synthesized by the methods described below. The reactions are performed in a solvent appropriate to the reagents and materials employed and suitable for the transformations. The functionality present on the molecule should be consistent with the transformations proposed. This will sometimes require a selection of a particular process scheme over another in order to obtain the desired compound of the invention. Preferred methods included, but are not limited to, those described below.

Compounds of Formula (II) can be prepared by an amide formation from compounds of Formula (IV) and a isonipecotic acid (piperidine-4-carboxylic acid, Va) derivative or nipecotic acid (piperidine-4-carboxylic acid, Vb) derivative, which should have the amino group protected, to give an intermediate of Formula (VI), followed by a deprotection of the amino group and a reduction of the amido group, as shown in Scheme 2. The commercially available acid derivatives (Va) and (Vb) with the amino group protected are those with a carbamate, such as BOC or CBZ, or with a benzyl group.

If Z=OH, the amidation can be performed by the activation of the carboxylic acid with a carbodiimide, such as 1,1-dicyclohexylcarbodiimide or 1-Ethyl 3-(3-dimethylamino propyl) carbodiimide, in the presence of a catalytic amount of an organic base, such as DMAP in an appropriate solvent, such as dichloromethane.

The amidation can also be achieved using piperidinecarbonyl chlorides, if Z=Cl, derived from isonipecotic acid or nipecotic acid in the presence of an aprotic solvent, but not limited to, such as dichloromethane and an organic base, such as diisopropylethylamine or triethylamine.

The acylation can also be performed starting from an ester derived from isonipecotic or nipecotic acid (Z=OR), when R is a good leaving group, such as p-nitrophenyl or ethyltrifluoroacetate using catalytic basic conditions Scheme 2

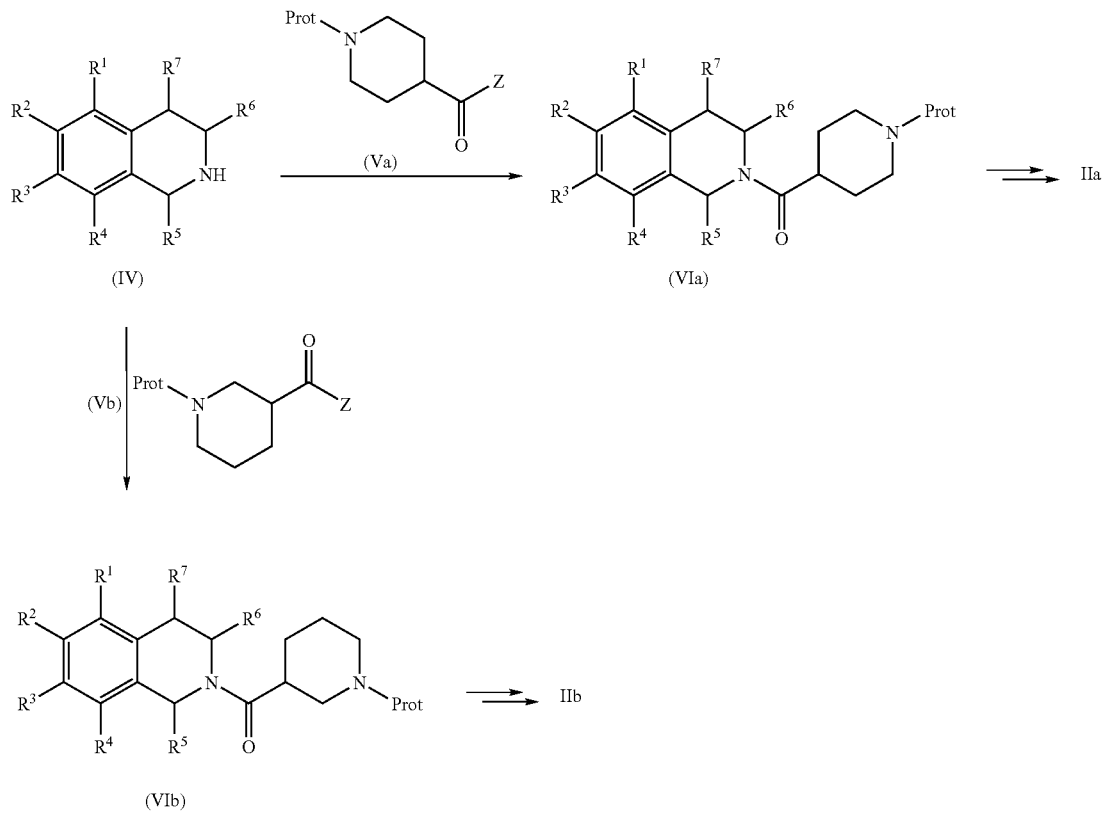

Before the reduction of the amido group, the deprotection of the amino group can be achieved by hydrolisis of the carbamate or by hydrogenation of the benzyl group using conventional methods. The reduction of the amido group can be performed in the presence of a hydride, such as LiAlH$_4$ or a borane in a dry polar aprotic solvent, such as tetrahydrofuran, as shown in Scheme 3.

Scheme 3

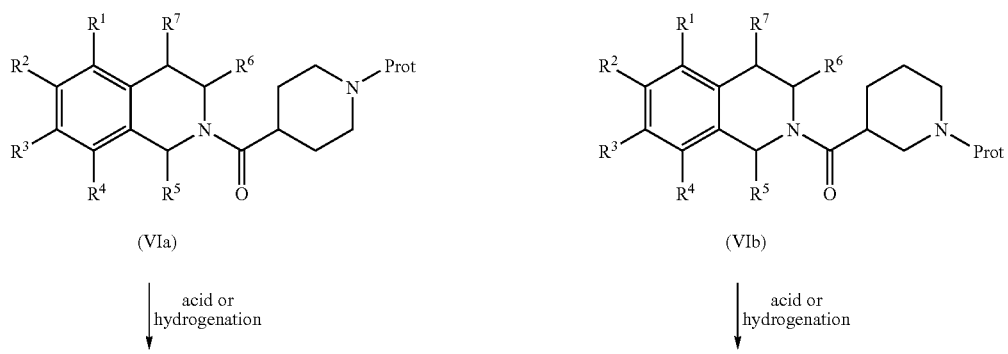

-continued

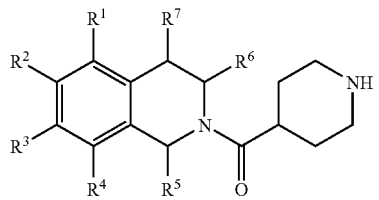

(VIIa)

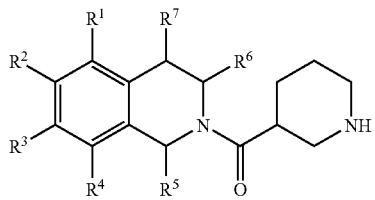

(VIIb)

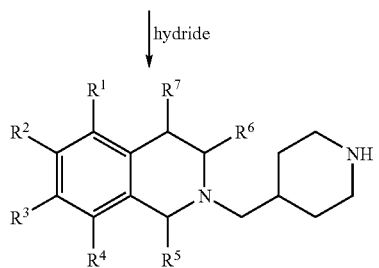

(IIa)

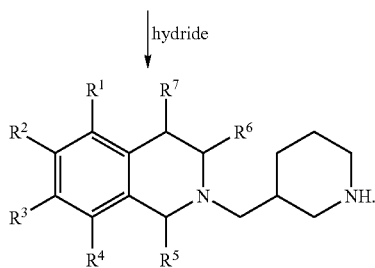

(IIb)

Where convenient, compounds of Formula (II) from compounds of Formula (VI) can be obtained by a reduction of the amido group before the deprotection of the amino group.

Compounds of Formula (II) can also be obtained by reductive amination of compounds of Formula (IV) with amino protected piperidinecarboaldehydes (VIIIa) or (VIIIb) in the presence of a hydride, such as NaBH(OAc)$_3$ (Scheme 4). The commercially available aldehydes (VIIIa) and (VIIIb) with the amino group protected are those with a carbamate, such as BOC or CBZ or with a benzyl group. The deprotection of the amino group by conventional methods can lead to desired compounds of Formula (II).

Scheme 4

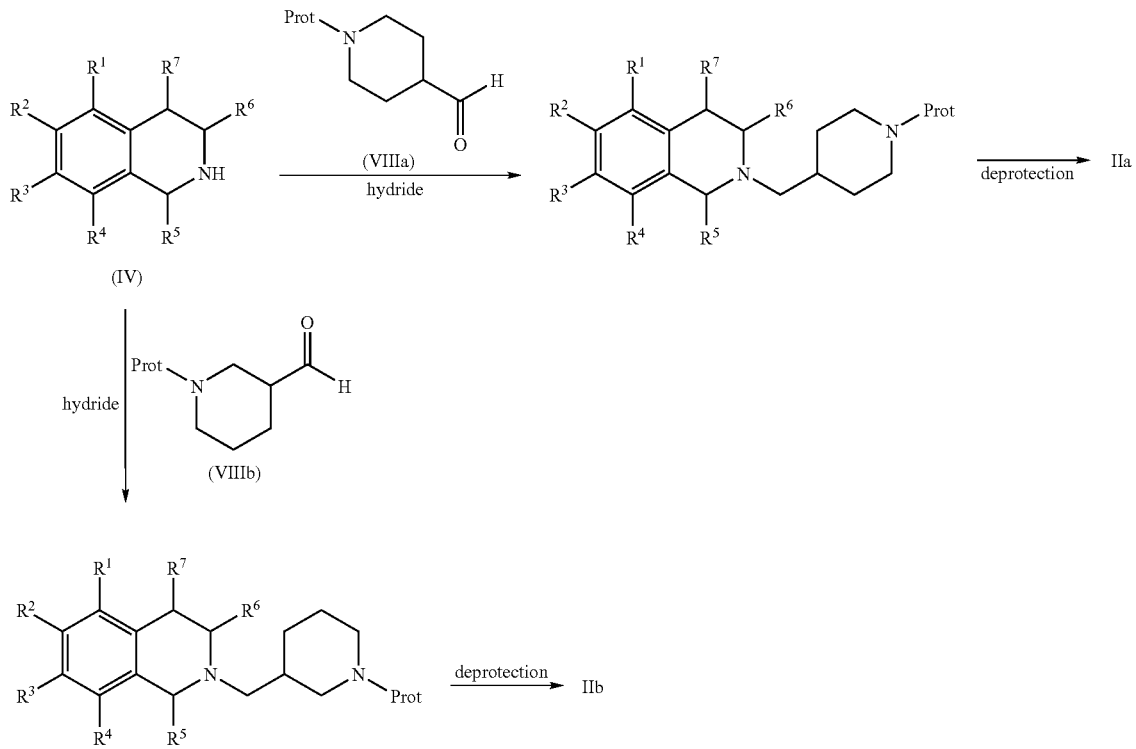

Compounds of Formula (II) can also be prepared by the alkylation of compounds of Formula (IV) with hydroxymethyl piperidines with the amino group protected (IXa) or (IXb), after a derivatization of the hydroxy group into a good leaving group Y (Xa) or (Xb).

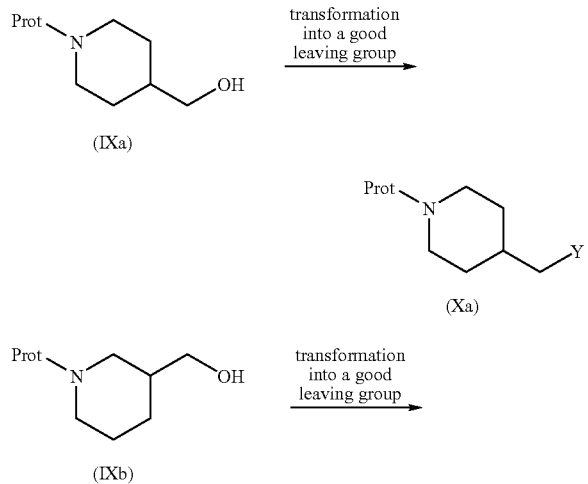

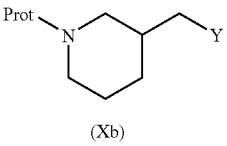

For example, the transformation of the hydroxy group into an alkyl or aryl sulfonate can be performed in the presence of a sulfonic anhydride, such as methanesulfonic anhydride in an organic aprotic solvent, such as dichloromethane or toluene and an organic base, such as triethylamine or diisopropylamine. The transformation can also be carried out with a sulfonic acid chloride in the presence of an aprotic solvent, such as dichloromethane in the presence of an organic base, such as diisopropylethylamine or triethylamine. Other transformations into a bromine, iodine or chlorine can be achieved by other conventional methods.

The alkylation of compounds of Formula (IV) with compounds of Formula (X) (Scheme 5) can be performed in the presence of an appropriate base and solvent. Useful bases include, but are not limited to, metal carbonates such as $K_2CO_3$ or $Cs_2CO_3$, metal hydroxides, hindered alkoxides or tertiary organic amines. Typical solvents include polar aprotic liquids such as DMF or THF, or protic liquids such as alcohols. The deprotection of the amino group can be afford by conventional methods.

Scheme 5

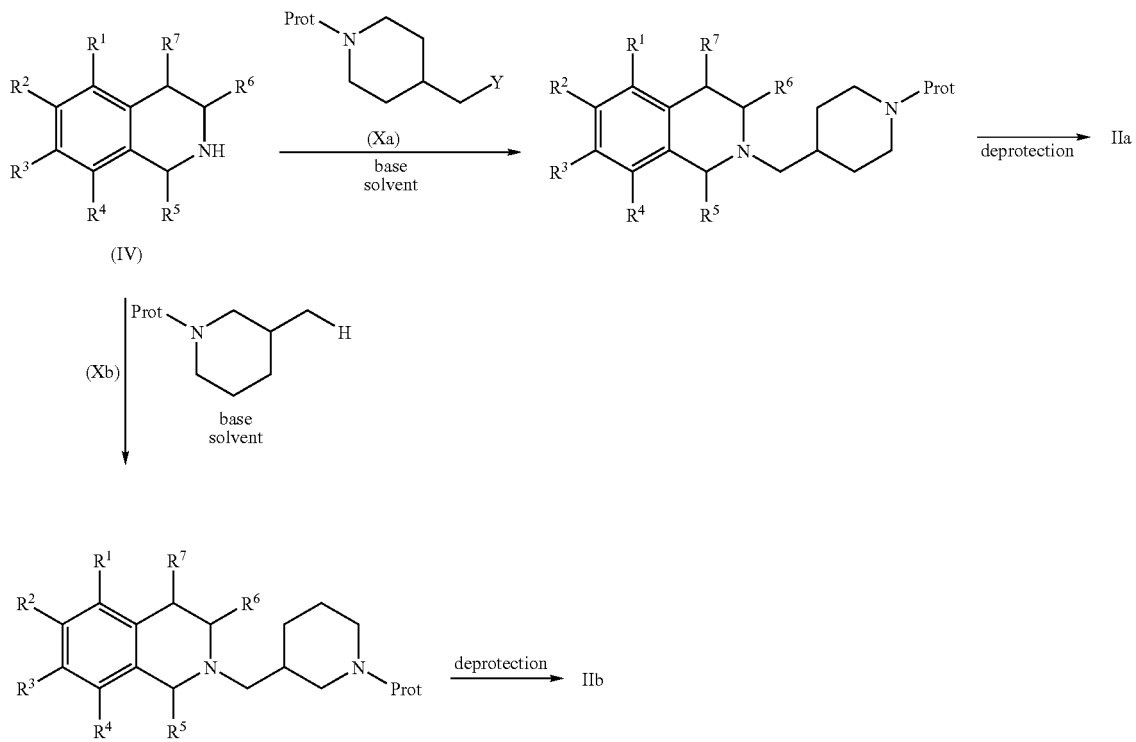

Some compounds of Formula (I) can also be prepared by the coupling of compounds of Formula (XIa) or (XIb) or their acid derivatives or by the coupling of compounds of Formula (XIc) or (XId):

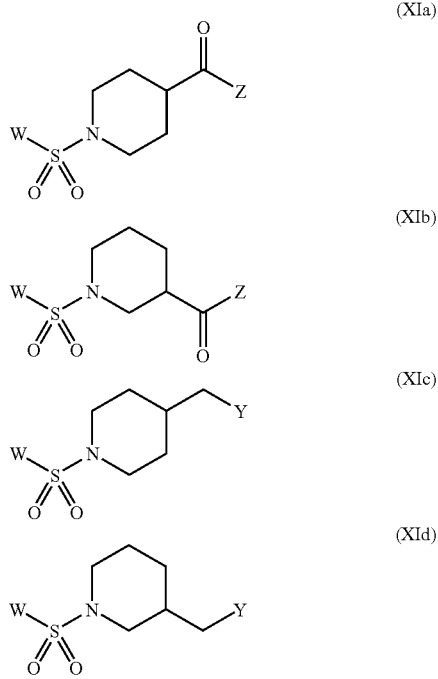

in which W is as defined in Formula (I), Z can be as it was described for compounds (Va) or (Vb) and Y can be as it was described for compounds (Xa) or (Xb), with a compound of a Formula (IV):

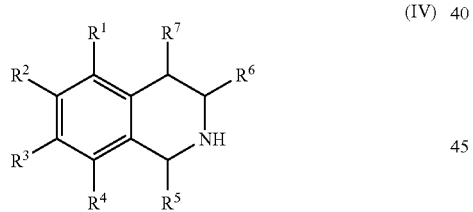

in which $R^1$-$R^7$ are as defined in Formula (I).

The coupling can be performed using the same methods and conditions described for the coupling of compounds of Formula (IV) with compounds of Formula (Va) or (Vb) and for the coupling of compounds of Formula (IV) with compounds of Formula (Xa) or (Xb).

Compound (IV) is prepared as it was described above. Compounds of Formula (XIa) and (XIb) can be synthesized by the coupling of isonipecotic and nipecotic acid with compounds of Formula (III) in an aprotic solvent, such as dichloromethane or toluene in the presence of an organic base, such as diisopropylethylamine or triethylamine. Compounds of Formula (XIc) and (XId) can be obtained from deprotected piperidines (Xa) and (Xb) by coupling with compounds of Formula (III) using similar conditions described above.

The obtained reaction products may, if desired, be purified by conventional methods, such as crystallisation, chromatography and trituration. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Another aspect of this invention relates to a method of treating or preventing an 5-$HT_7$ mediated disease which method comprises administering to a patient in need of such a treatment a therapeutically effective amount of a compound of formula (I) or a pharmaceutical composition thereof. Among the 5-$HT_7$ mediated diseases that can be treated are diseases caused by failures in central and peripheral serotonin-controlling functions, such as pain, sleep disorder, shift worker syndrome, jet lag, depression, seasonal affective disorder, migraine, anxiethy, psychosis, schizophrenia, cognition and memory disorders, neuronal degeneration resulting from ischemic events, cardiovascular diseases such as hypertension, irritable bowel syndrome, inflammatory bowel disease, spastic colon or urinary incontinence.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

The following examples are given only as further illustration of the invention, they should not be taken as a definition of the limits of the invention.

EXAMPLES

The starting materials of general formula (I) were prepared by means of conventional organic chemistry methods known to those skilled in the art. The preparation of some of the intermediates of general formulas (II), (IV), (VI) and (VII) is shown below:

Example A

This example illustrate the preparation of a compounds of general formula (IV).

6-methoxy-1,2,3,4-tetrahydroisoquinoline hydrochloride.

This compound is well described in the literature in the Organic Reactions 1951, Vol. 6 (Chapter 3, pages 151-190).

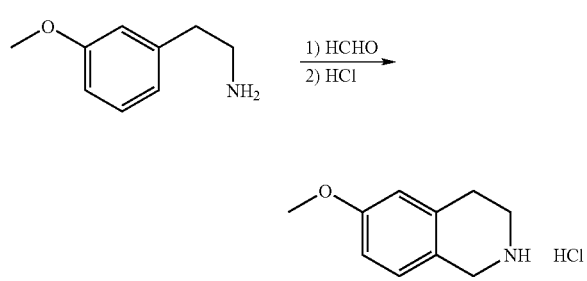

A solution of 35% formaldehyde (2.49 g, 0.034 mol) was added dropwise to 2-(3-methoxyphenyl)ethanamine (5 g, 0.033 mol). The warm solution soon deposited an oil and the reaction was completed by heating the mixture for one hour at 100° C. The oil was extracted with toluene (25 ml) and washed with water (3×18 ml). The extract was dried over $Na_2SO_4$ and the solvent was concentrated to yield a yellow oil. A solution of 20% hydrochloric acid (6 ml) was added to the crude and the mixture was stirred at 100° C. for 1 hour. After the evaporation to dryness, the residue was dissolved in a little water, made alkaline with concentrated potassium hydroxide, extracted with dichloromethane (3×90 ml) and dried over $Na_2SO_4$. After the evaporation of the solvent, the oil was dissolved in ethyl acetate and concentrated hydrochloric acid was added to form the hydrochloride, which was filtered to yield a white solid identified as 6-methoxy-1,2,3,4-tetrahydroisoquinoline hydrochloride (5.1 g, 80% yield).

$^1$H NMR (300 MHz, CHLOROFORM-D) δ ppm 2.80 (t, J=6.01 Hz, 2H) 3.14 (t, J=6.01 Hz, 2H) 3.78 (s, 3H) 3.97 (s, 2H) 6.63 (d, J=2.50 Hz, 1H) 6.71 (dd, J=8.42, 2.56 Hz, 1 H) 6.93 (d, J=8.42 Hz, 1H)

MS (APCI (M+H)$^+$): 164

Example B

This example illustrate the preparation of a compound of general formula (VI).

4-(6,7-Dimethoxy-3,4-dihydro-1H-isoquinoline-2-carbonyl)-piperidine-1-carboxylic acid tert-butyl ester.

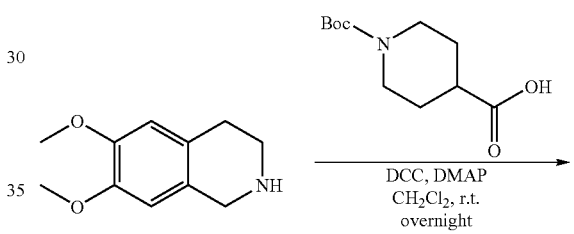

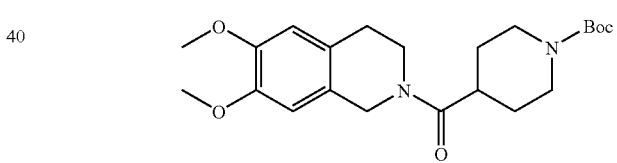

DCC (2.16 g, 0.011 mol), a catalytic amount of DMAP (0.098 g, 8 mmol) and 1-(tert-butoxycarbonyl)piperidine-4-carboxylic acid (2.04 g, 0.009 mol) were added to a solution of 6,7-Dimethoxy-1,2,3,4-tetrahydroisoquinoline (1.31 g, 0.008 mol) in dichloromethane (30 ml). The clear solution soon deposited a white solid corresponding to the cyclohexyl urea formation. The crude was stirred for 2 hours at room temperature. The solid was filtered and the crude was washed with water and dried over $Na_2SO_4$. The solvent was vacuum concentrated and the residue was purified by flash chromatography using a gradient consisting of different mixtures of dichloromethane/methanol to give pure tert-Butyl-4-(6,7-dimethoxy-1,2,3,4-tetrahydroisoquinoline-2-carbonyl)piperidine-1-carboxylate as yellow solid (3.8 g, 85% yield).

$^1$H NMR (300 MHz, CHLOROFORM-D) δ ppm 1.45 (s, 9H) 1.62 (m, 4H) 1.70 (m, 4H) 2.78 (m, 3H) 3.72 (m, 1H) 3.86 (s, 6H) 4.16 (m, 2H) 4.64 (s, 1H) 6.62 (s, 2H)

MS (APCI (M+H)$^+$): 405

Example C

This example illustrate the preparation of a compound of general formula (VII).

(6,7-Dimethoxy-3,4-dihydro-1H-isoquinolin-2-yl)-piperidin-4-yl-methanone.

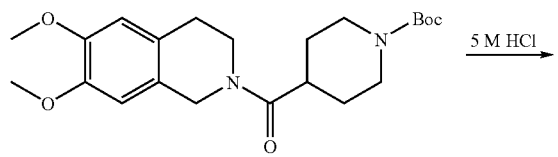

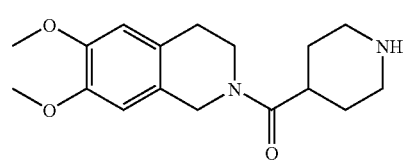

A solution of 5 N hydrochloric acid in ether (5 ml) was added to a solution of 4-(6,7-Dimethoxy-3,4-dihydro-1H-isoquinoline-2-carbonyl)-piperidine-1-carboxylic acid tert-butyl ester (3 g, 7.43 mmol) in ethyl acetate and the mixture was stirred for 2 hours at room temperature. The precipitate formed was collected by filtration and the white solid obtained was indetified as (6,7-dimethoxy-3,4-dihydroisoquinolin-2(1H)-yl)(piperidin-4-yl)-methanone (2.1 g, 95% yield).

MS (APCI (M+H)$^+$): 305

Example D

This example illustrate the preparation of a compound of general formula (II).

6,7-dimethoxy-2-(piperidin-4-ylmethyl)-1,2,3,4-tetrahydroisoquinoline.

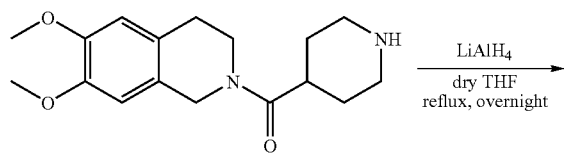

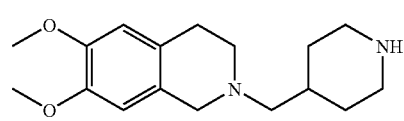

A 1 M solution of LiAlH$_4$ in dry tetrahydrofuran (12 ml) was added dropwise to a solution of (6,7-dimethoxy-3,4-dihydroisoquinolin-2(1H)-yl)(piperidin-4-yl)methanone (2 g, 6.6 mmol) in dry tetrahydrofuran (60 ml) under argon atmosphere. The mixture was refluxed overnight. Water was added to the crude, made alkaline with 1 N NaOH and the salts formed was filtered over celite. Extraction with ethyl acetate yielded a solution that was dried with Na$_2$SO$_4$ and concentrated in vacuo to give and oil that was purified by flash chromatography.

MS (APCI (M+H)$^+$): 291

Example E

This example illustrate the preparation of a compound of general formula (I).

2-((1-(2,5-dichlorophenylsulfonyl)piperidin-4-yl)methyl)-1,2,3,4-tetrahydroisoquino-line.

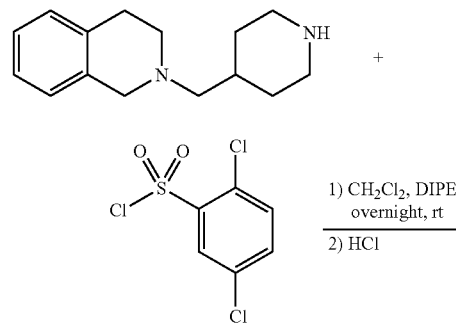

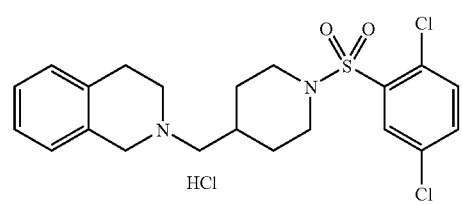

2,5-dichlorobenzene-1-sulfonyl chloride (108.1 mg, 0.44 mmol) was added to a solution of 2-(piperidin-4-ylmethyl)-1,2,3,4-tetrahydroisoquinoline dihydrochloride (92.1 mg, 0.40 mmol) and N,N-diisopropylethylamine (206.9.2 mg, 1.60 mmol) in CH$_2$Cl$_2$ (10 mL) and the mixture was stirred overnight at room temperature. The resulting solution was washed with water (3×10 mL), dried over Na$_2$SO$_4$, and evaporated to dryness. The free base was dissolved in ethyl acetate (1 ml). A 2.8 M solution of hydrogen chloride in ethanol (0.10 mL) was then added. The product was crystallized and collected by filtration, and vacuum dried to give a white solid (138 mg, 78%).

$^1$H NMR (300 MHz, DMSO-D6) δ ppm 1.21 (m, 2H) 1.90 (m, 2H) 2.08 (m, 1H) 2.76 (m, 2H) 3.01 (m, 1H) 3.10 (m, 2H) 3.24 (m, 2H) 3.65 (m, 1H) 3.75 (d, J=12.45 Hz, 2H) 4.23 (dd, J=15.30, 7.83 Hz, 1H) 4.53 (d, J=14.94 Hz, 1H) 7.15 (m, 1H) 7.24 (m, 3H) 7.77 (m, 2H) 7.94 (m, 1H) 10.22 (br, 1H)

MS (APCI (M+H)$^+$): 439

The spectroscopic data for the identification of some of the sulfonamides compounds of the invention having general formula (I), prepared analogously to the methods described in the above examples, are shown in the following table 1:

| No | STRUCTURE | Autonom | ¹H-NMR | MS (APCI (M + H)⁺) |
|----|-----------|---------|--------|--------------------|
| 1 | 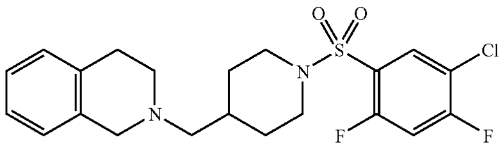 | 2-[1-(5-Chloro-2,4-difluoro-benzene sulfonyl)-piperidin-4-ylmethyl]-1,2,3,4-tetrahydroisoquinoline hydrochloride | 1H NMR (300 MHz, DMSO-D6) δ ppm 1.23 (m, 2H) 1.91 (m, 3H) 2.58 (t, J=11.57 Hz, 2H) 3.00 (m, 1H) 3.09 (m, 2H) 3.24 (m, 2H) 3.68 (m, 3H) 4.21 (m, 1H) 4.51 (d, J=14.06 Hz, 1H) 7.15 (m, 1H) 7.23 (m, 3H) 7.96 (m, 2H) 10.24 (br, 1H) | 441 |
| 2 | 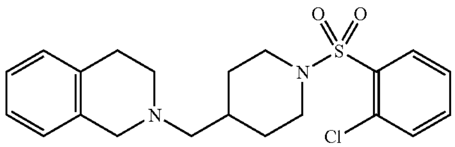 | 2-[1-(2-Chloro-benzenesulfonyl)-piperidin-4-ylmethyl]-1,2,3,4-tetrahydro-isoquinoline hydrochloride | 1H NMR (300 MHz, DMSO-D6) δ ppm 1.23 (m, 2H) 1.90 (m, 2H) 2.06 (m, 1H) 2.71 (m, 2H) 3.01 (m, 1H) 3.09 (m, 2H) 3.19 (m, 2H) 3.69 (m, 3H) 4.23 (m, 1H) 4.52 (d, J=16.11 Hz, 1H) 7.15 (m, 1H) 7.24 (m, 3H) 7.56 (m, 1H) 7.70 (m, 2H) 7.97 (d, J=7.91 Hz, 1H) 10.19 (br, 1H) | 405 |
| 3 | 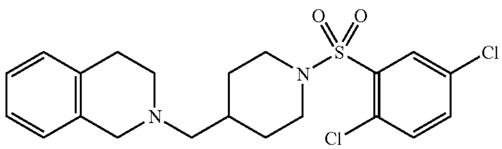 | 2-[1-(2,5-Dichloro-benzenesulfonyl)-piperidin-4-ylmethyl]-1,2,3,4-tetrahydro-isoquinoline hydrochloride | 1H NMR (300 MHz, DMSO-D6) δ ppm 1.21 (m, 2H) 1.90 (m, 2H) 2.08 (m, 1H) 2.76 (m, 2H) 3.01 (m, 1H) 3.10 (m, 2H) 3.24 (m, 2H) 3.65 (m, 1H) 3.75 (d, J=12.45 Hz, 2H) 4.23 (dd, J=15.30, 7.83 Hz, 1H) 4.53 (d, J=14.94 Hz, 1H) 7.15 (m, 1H) 7.24 (m, 3H) 7.77 (m, 2H) 7.94 (m, 1H) 10.22 (br, 1H) | 439 |
| 4 | 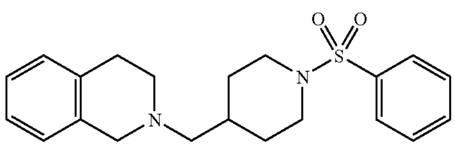 | 2-(1-Benzenesulfonyl-piperidin-4-yl methyl)-1,2,3,4-tetrahydroisoquinoline hydrochloride | | 371 |
| 5 | 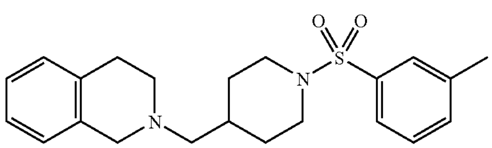 | 2-[1-(Toluene-3-sulfonyl)-piperidin-4-ylmethyl]-1,2,3,4-tetrahydroisoquinoline hydrochloride | 1H NMR (300 MHz, DMSO-D6) δ ppm 1.24 (m, 2H) 1.89 (m, 3H) 2.18 (t, J=11.27 Hz, 2H) 2.40 (s, 3H) 2.97 (m, 1H) 3.04 (m, 2H) 3.22 (m, 2H) 3.61 (m, 3H) 4.19 (m, 1H) 4.49 (d, J=12.01 Hz, 1H) 7.11 (m, 1H) 7.21 (m, 3H) 7.52 (m, 4H) 10.18 1H) | 385 |
| 6 | 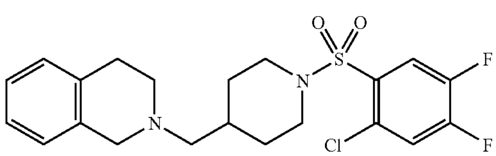 | 2-[1-(2-Chloro-4,5-difluoro-benzene-sulfonyl)-piperidin-4-ylmethyl]-1,2,3,4-tetrahydroisoquinoline hydrochloride | 1H NMR (300 MHz, DMSO-D6) δ ppm 1.21 (m, 2H) 1.88 (m, 2H) 2.05 (m, 1H) 2.77 (m, 2H) 3.01 (m, 1H) 3.09 (m, 2H) 3.25 (m, 2H) 3.63 (m, 1H) 3.73 (d, J=12.30 Hz, 2H) 4.22 (dd, J=16.03, 7.10 Hz, 1H) 4.52 (d, J=13.62 Hz, 1H) 7.15 (m, 1H) 7.23 (m, 3H) 8.05 (m, 2H) 10.26 (br, 1H) | 441 |
| 7 | 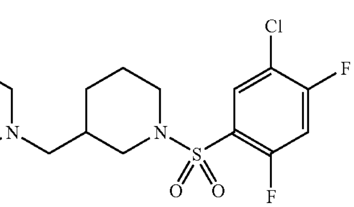 | 2-[1-(5-Chloro-2,4-difluoro-benzene-sulfonyl)-piperidin-3-ylmethyl]-1,2,3,4-tetrahydroisoquinoline hydrochloride | | 441 |
| 8 | 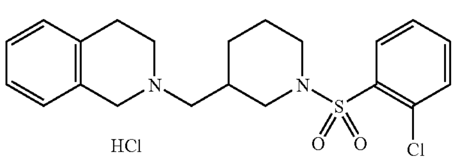 | 2-[1-(2-Chloro-benzenesulfonyl)-piperidin-3-ylmethyl]-1,2,3,4-tetrahydro-isoquinoline hydrochloride | | 405 |

-continued

| No | STRUCTURE | Autonom | ¹H-NMR | MS (APCI (M + H)⁺) |
|---|---|---|---|---|
| 9 | 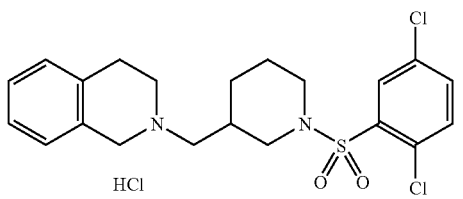 | 2-[1-(2,5-Dichloro-benzenesulfonyl)-piperidin-3-ylmethyl]-1,2,3,4-tetrahydro-isoquinoline hydrochloride | | 439 |
| 10 | 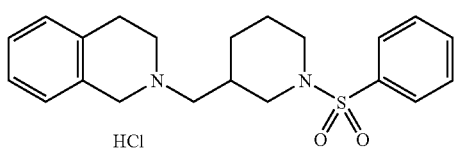 | 2-(1-Benzenesulfonyl-piperidin-3-ylmethyl)-1,2,3,4-tetrahydro-isoquinoline hydrochloride | | 371 |
| 11 | 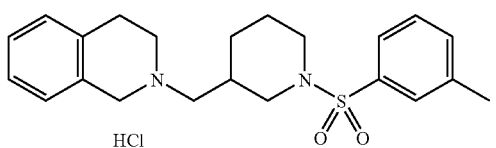 | 2-[1-(Toluene-3-sulfonyl)-piperidin-3-ylmethyl]-1,2,3,4tetra-hydroiso-quinoline hydrochloride | 1H NMR (300 MHz, DMSO-D6) δ ppm 1.23 (m, 2H) 1.72 (m, 2H) 2.18 (m, 1H) 2.27 (m, 2H) 2.40 (s, 3H) 3.04 (m, 3H) 3.21 (m, 2H) 3.69 (m, 3H) 4.21 (m, 1H) 4.55 (m, 1H) 7.25 (m, 4H) 7.52 (m, 3H) 7.55 (m, 1H) 10.22 (br, 1H) | 385 |
| 12 | 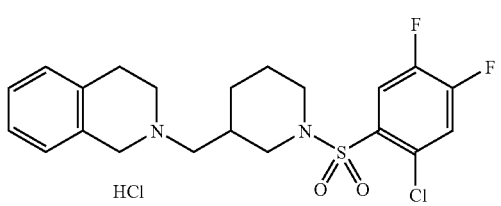 | 2-[1-(2-Chloro-4,5-difluoro-benzene sulfonyl)-piperidin-3-ylmethyl]-1,2,3,4-tetrahydroisoquinoline hydrochloride | | 441 |
| 13 | 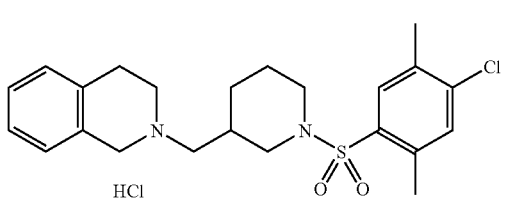 | 2-[1-(4-Chloro-2,5-dimethyl-benzene sulfonyl)-piperidin-3-ylmethyl]-1,2,3,4-tetrahydroisoquinoline hydrochloride | | 433 |
| 14 | 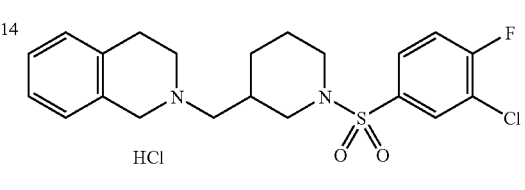 | 2-[1-(3-Chloro-4-fluorobenzene-sulfonyl)-piperidin-3-ylmethyl]-1,2,3,4-tetrahydroisoquinoline hydrochloride | 1H NMR (300 MHz, DMSO-D6) δ ppm 1.09 (m, 1H) 1.55 (m, 1H) 1.72 (m, 2H) 2.23 (d, J=8.64 Hz, 2H) 2.42 (m, 1H) 3.08 (m, 3H) 3.23 (m, 2H) 3.44 (m, 1H) 3.68 (m, 2H) 4.27 (dd, J=16.03, 7.39 Hz, 1H) 4.55 (m, 1H) 7.26 (m, 4H) 7.75 (m, 2H) 7.95 (m, 1H) 10.32 (br, 1H) | 423 |
| 15 | 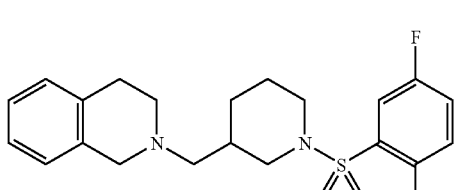 | 2-[1-(5-Fluoro-2-methyl-benzene-sulfonyl)-piperidin-3-ylmethyl]-1,2,3,4-tetrahydroisoquinoline hydrochloride | | 403 |
| 16 | 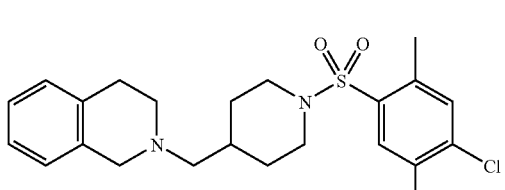 | 2-[1-(4-Chloro-2,5-dimethyl-benzene sulfonyl)-piperidin-4-ylmethyl]-1,2,3,4-tetrahydroisoquinoline hydrochloride | 1H NMR (300 MHz, DMSO-D6) δ ppm 1.22 (m, 2H) 1.90 (m, 2H) 2.04 (m, 1H) 2.36 (s, 3H) 2.50 (s, 3H) 2.55 (m, 2H) 3.01 (m, 1H) 3.09 (m, 2H) 3.25 (m, 2H) 3.63 (m, 3H) 4.22 (dd, J=15.45, 7.83 Hz, 1H) 4.52 (d, J=15.67 Hz, 1H) 7.15 (m, 1H) 7.24 (m, 3H) 7.57 (s, 1H) 7.75 (s, 1H) 10.28 (br, 1H) | 433 |

-continued

| No | STRUCTURE | Autonom | ¹H-NMR | MS (APCI (M + H)⁺) |
|---|---|---|---|---|
| 17 | 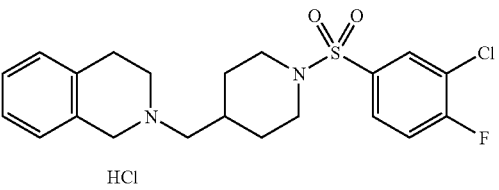 | 2-[1-(3-Chloro-4-fluoro-benzenesulfonyl)-piperidin-4-ylmethyl]-1,2,3,4-tetrahydroisoquinoline hydrochloride | | 423 |
| 18 | 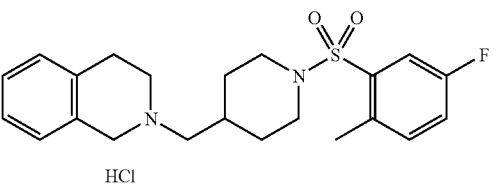 | 2-[1-(5-Fluoro-2-methyl-benzene-sulfonyl)-piperidin-4-ylmethyl]-1,2,3,4-tetrahydroisoquinoline hydrochloride | | 403 |
| 19 | 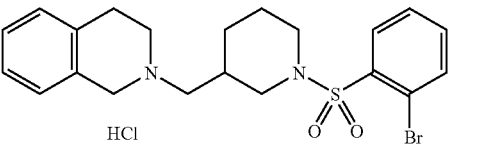 | 2-[1-(2-Bromo-benzenesulfonyl)-piperidin-3-ylmethyl]-1,2,3,4-tetrahydro-isoquinoline hydrochloride | | 449 |
| 20 | 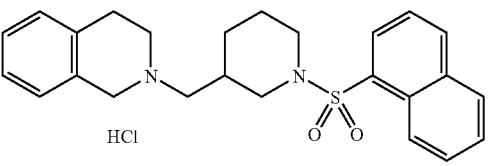 | 2-[1-(Naphthalene-1-sulfonyl)-piperidin-3-ylmethyl]-1,2,3,4-tetrahydroisoquinoline hydrochloride | | 421 |
| 21 | 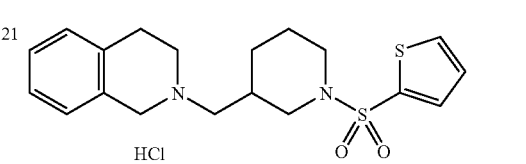 | 2-[1-(Thiophene-2-sulfonyl)-piperidin-3-ylmethyl]-1,2,3,4-tetrahydroisoquinoline hydrochloride | | 377 |
| 22 | 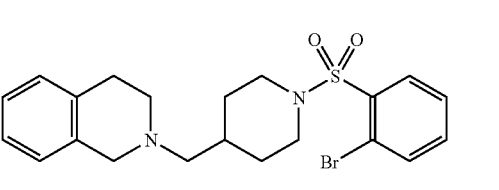 | 2-[1-(2-Bromo-benzenesulfonyl)-piperidin-4-ylmethyl]-1,2,3,4-tetrahydro-isoquinoline hydrochloride | 1H NMR (300 MHz, DMSO-D6) δ ppm 1.23 (m, 2H) 1.89 (m, 2H) 2.06 (m, 1H) 2.74 (m, 2H) 3.02 (m, 1H) 3.10 (m, 2H) 3.26 (m, 2H) 3.69 (m, 3H) 4.24 (m, 1H) 4.53 (d, J=16.72 Hz, 1H) 7.16 (m, 1H) 7.23 (m, 3H) 7.58 (qd, J=7.10, 1.68 Hz, 2H) 7.88 (dd, J=7.82, 1.76 Hz, 1H) 7.99 (dd, J=7.47, 2.05 Hz, 1H) 10.13 (br, 1H) | 449 |
| 23 | 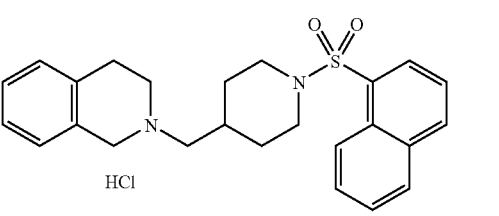 | 2-[1-(Naphtalene-1-sulfonyl)-piperidin-4-ylmethyl]-1,2,3,4-tetrahydroisoquinoline hydrochloride | 1H NMR (300 MHz, DMSO-D6) δ ppm 1.22 (m, 1H) 1.92 (m, 3H) 2.44 (m, 2H) 2.97 (m, 1H) 3.03 (m, 2H) 3.19 (m, 2H) 3.59 (m, 1H) 3.75 (m, 2H) 4.17 (dd, J=15.23, 5.86 Hz, 1H) 4.47 (d, J=17.28 Hz, 1H) 7.10 (m, 1H) 7.20 (m, 3H) 7.70 (m, 3H) 8.12 (t, J=7.83 Hz, 2H) 8.29 (d, J=8.05 Hz, 1H) 8.68 (d, J=8.49 Hz, 1H) 10.13 (br, 1H) | 421 |
| 24 | 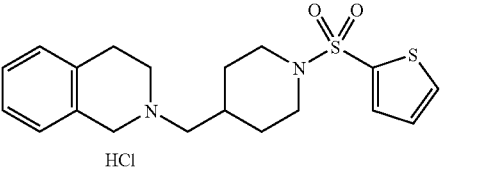 | 2-[1-(Thiophene-2-sulfonyl)-piperidin-4-ylmethyl]-1,2,3,4-tetrahydroisoquinoline hydrochloride | | 377 |

-continued

| No | STRUCTURE | Autonom | ¹H-NMR | MS (APCI (M + H)⁺) |
|---|---|---|---|---|
| 25 | 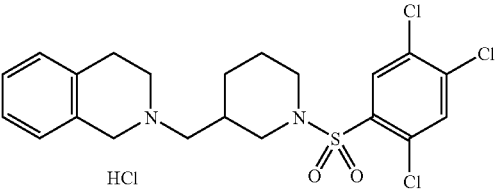 | 2-[1-(2,4,5-Trichloro-benzenesulfonyl)-piperidin-3-ylmethyl]-1,2,3,4-tetrahydro-isoquinoline hydrochloride | | 473 |
| 26 | 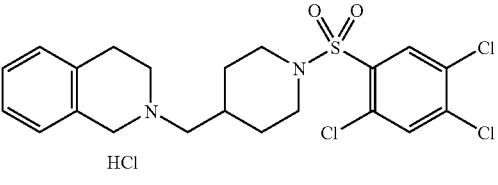 | 2-[1-(2,4,5-Trichloro-benzenesulfonyl)-piperidin-4-ylmethyl]-1,2,3,4-tetrahydro-isoquinoline hydrochloride | 1H NMR (300 MHz, DMSO-D6) δ ppm 1.21 (m, 1H) 1.89 (m, 2H) 2.06 (m, 1H) 2.78 (m, 2H) 3.02 (m, 1H) 3.10 (m, 2H) 3.26 (m, 2H) 3.63 (m, 1H) 3.75 (d, J=12.45 Hz, 2H) 4.23 (dd, J=15.37, 6.74 Hz, 1H) 4.52 (m, 1H) 7.16 (m, 1H) 7.24 (m, 3H) 8.10 (s, 1H) 8.18 (s, 1H) 10.13 (br 1H) | 473 |
| 27 | 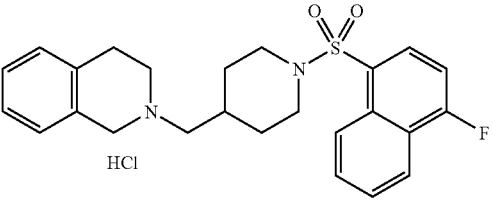 | 2-[1-(4-Fluoro-naphtalene-1-sulfonyl)-piperidin-4-ylmethyl]-1,2,3,4-tetrahydro-isoquinoline hydrochloride | | 439 |
| 28 | 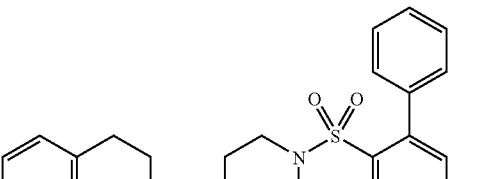 | 2-[1-(Biphenyl-2-sulfonyl)-piperidin-4-ylmethyl]-1,2,3,4-tetrahydroisoquinoline hydrochloride | | 447 |
| 29 | 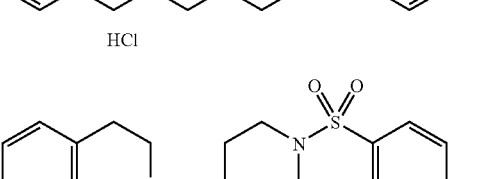 | 2-[1-(2,3-Dihydro-benzofuran-5-sulfonyl)-piperidin-4-ylmethyl]-1,2,3,4-tetrahydro-isoquinoline hydrochloride | | 413 |
| 30 | 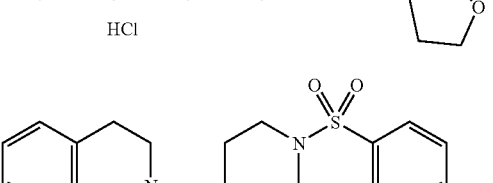 | 2-[1-(Dibenzofuran-2-sulfonyl)-piperidin-4-ylmethyl]-1,2,3,4-tetrahydroisoquinoline hydrochloride | | 461 |
| 31 | 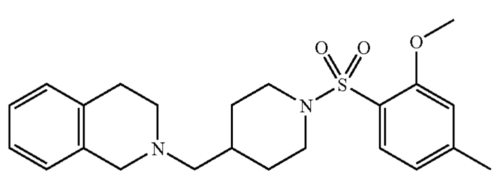 | 2-[1-(2-Methoxy-4-methyl-benzenesulfonyl)-piperidin-4-ylmethyl]-1,2,3,4-tetrahydro-isoquinoline hydrochloride | | 415 |

| No | STRUCTURE | Autonom | ¹H-NMR | MS (APCI) (M + H)⁺ |
|---|---|---|---|---|
| 32 | 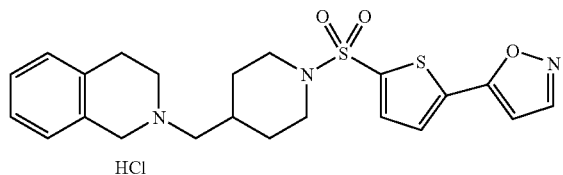 | 2-[1-(5-Isoxazol-5-yl-thiophene-2-sulfonyl)-piperidin-4-ylmethyl]-1,2,3,4-tetrahydroisoquinoline hydrochloride | | 444 |
| 33 | 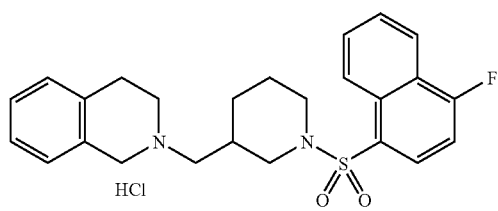 | 2-[1-(4-Fluoro-naphtalene-1-sulfonyl)-piperidin-3-ylmethyl]-1,2,3,4-tetrahydro-isoquinoline hydrochloride | | 439 |
| 34 | 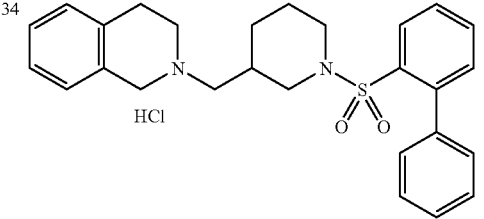 | 2-[1-(Biphenyl-2-sulfonyl)-piperidin-3-ylmethyl]-1,2,3,4-tetrahydroisoquinoline hydrochloride | | 447 |
| 35 | 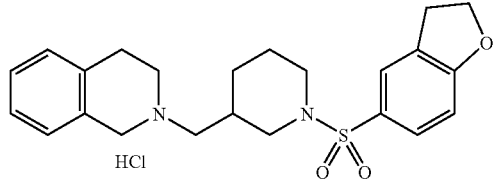 | 2-[1-(2,3-Dihydro-benzofuran-5-sulfonyl)-piperidin-3-ylmethyl]-1,2,3,4-tetrahydro-isoquinoline hydrochloride | | 413 |
| 36 | 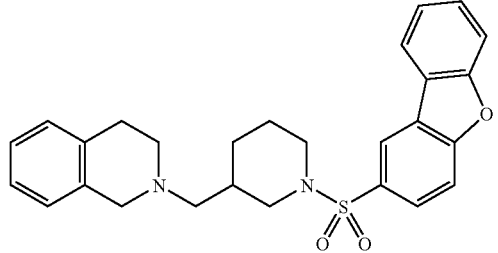 | 2-[1-(Dibenzofuran-2-sulfonyl)-piperidin-3-ylmethyl]-1,2,3,4-tetrahydroisoquinoline | | 461 |
| 37 | 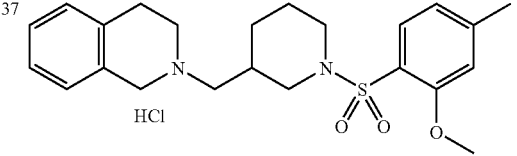 | 2-[1-(2-Methoxy-4-methyl-benzene-sulfonyl)-piperidin-3-ylmethyl]-1,2,3,4-tetrahydro-isoquinoline hydrochloride | | 415 |
| 38 | 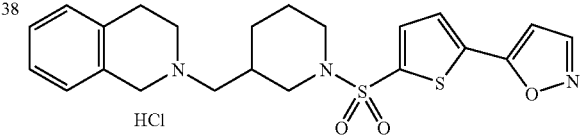 | 2-[1-(5-Isoxazol-5-yl-thiophene-2-sulfonyl)-piperidin-3-ylmethyl]-1,2,3,4-tetrahydroiso-quinoline hydrochloride | | 444 |

-continued

| No | STRUCTURE | Autonom | ¹H-NMR | MS (APCI (M + H)⁺) |
|---|---|---|---|---|
| 39 | 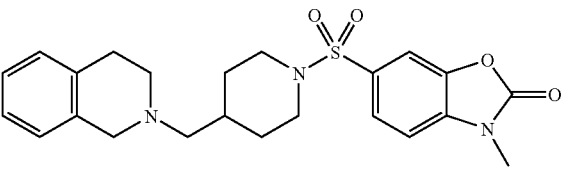 | 6-[4-(3,4-Dihydro-1H-isoquinolin-2-yl-methyl)-piperidine-1-sulfonyl]-3H-benzooxazol-2-one | | 442 |
| 40 | 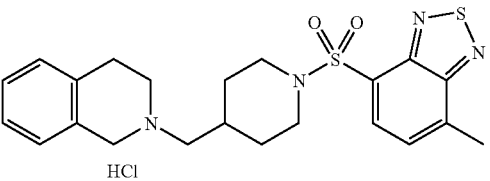 | 2-[1-(7-Methyl-benzo[1,2,5]-thiadiazole-4-sulfonyl)-piperidin-4-ylmethyl]-1,2,3,4-tetrahydroisoquinoline hydrochloride | | 443 |
| 41 | 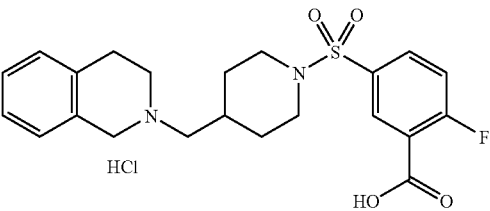 | 5-[4-(3,4-Dihydro-1H-isoquinolin-2-yl-methyl)-piperidine-1-sulfonyl]-2-fluoro-benzoic acid hydrochloride | | 433 |
| 42 | 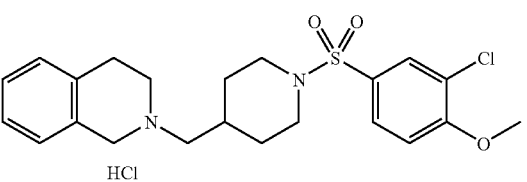 | 2-[1-(3Cloro-4-methoxy-benzene-sulfonyl)-piperidin-4-ylmethyl]-1,2,3,4-tetrahydro-isoquinoline hydrochloride | | 435 |
| 43 | 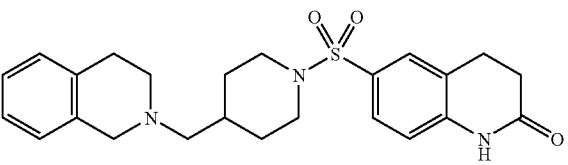 | 6-[4-(3,4-Dihydro-1H-4isoquinolin-2-yl-methyl)-piperidine-1-sulfonyl]-3,4-dihydro-1H-quinolin-2-one | | 440 |
| 44 | 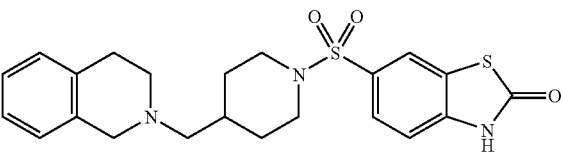 | 6-[4-(3,4-Dihydro-1H-isoquinolin-2-yl-methyl)-piperidine-1-sulfonyl]-3H-benzothiazol-2-one | | 444 |
| 45 | 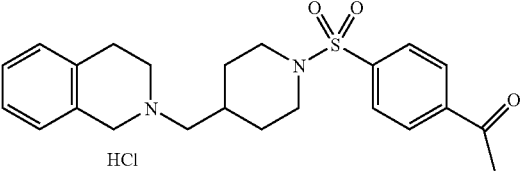 | 1{4-[4-(3,4-Dihydro-1H-isoquinolin-2-yl-methyl)-piperidine-1-sulfonyl]-phenyl}-ethanone hydrochloride | | 413 |
| 46 | 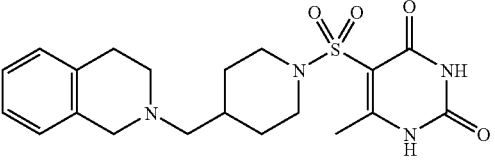 | 5-[4-(3,4-Dihydro-1H-isoquinolin-2-yl-methyl)-piperidine-1-sulfonyl]-6-methyl-1H-pyrimidine-2,4-dione | | 419 |

| No | STRUCTURE | Autonom | ¹H-NMR | MS (APCI) (M + H)⁺ |
|---|---|---|---|---|
| 47 | 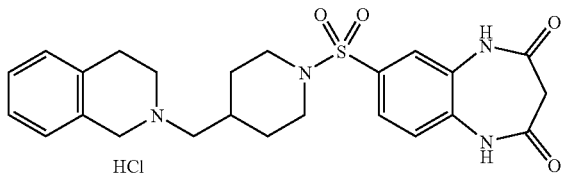 | 7-[4-(3,4-Dihydro-1H-isoquinolin-2-yl-methyl)-piperidine-1-sulfonyl]-1,5-dihydrobenzo[b][1,4]-diazepine-2-dione hydrochloride | | 469 |
| 48 | 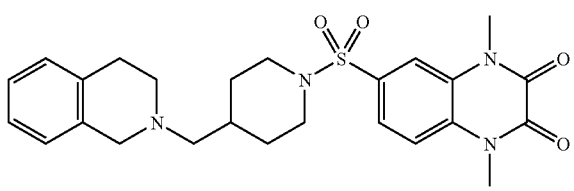 | 6-[4-(3,4-Dihydro-1H-isoquinolin-2-yl-methyl)-piperidine-1-sulfonyl]-1,4-dimethyl-1,4-dihydroquinoxaline-2,3-dione | | 483 |
| 49 | 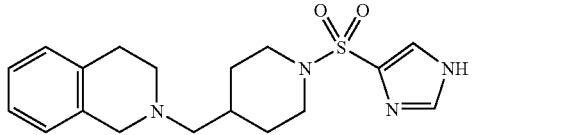 | 2-[1-(1H-Imidazole-4-sulfonyl)-piperidin-4-ylmethyl]-1,2,3,4-tetrahydro-isoquinoline | | 361 |
| 50 | 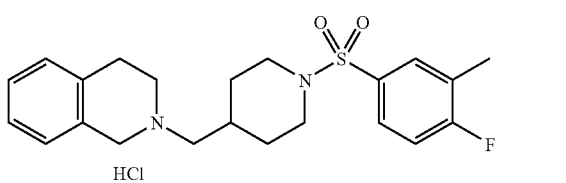 | 2-[1-(4-Fluoro-3-methyl-benzene-sulfonyl)-piperidin-4-ylmethyl]-1,2,3,4-tetrahydro-isoquinoline hydrochloride | | 399 |
| 51 | 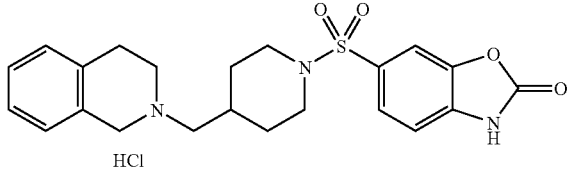 | 6-[4-(3,4-Dihydro-1H-isoquinolin-2-yl-methyl)-piperidine-1-sulfonyl]-3H-benzooxazol-2-one hydrochloride | | 428 |
| 52 | 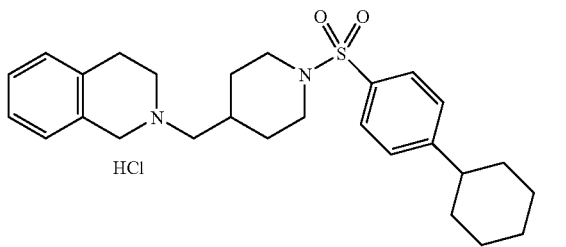 | 2-[1-(4-Cyclohexyl-benzenesulfonyl)-piperidin-4-ylmethyl]-1,2,3,4-tetrahydro-isoquinoline hydrochloride | | 453 |
| 53 | 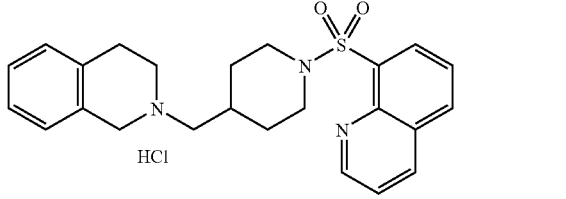 | 8-[4-(3,4-Dihydro-1H-isoquinolin-2-yl-methyl)-piperidine-1-sulfonyl]-quinoline hydrochloride | | 422 |

-continued

| No | STRUCTURE | Autonom | ¹H-NMR | MS (APCI (M + H)⁺) |
|---|---|---|---|---|
| 54 | 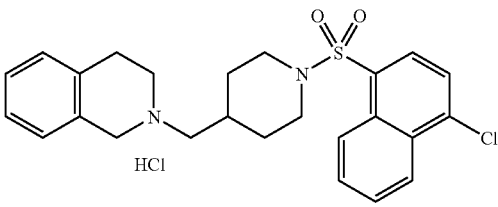 | 2-[1-(4-Chloro-naphtalene-1-sulfonyl)-piperidin-4-ylmethyl]-1,2,3,4-tetrahydro-isoquinoline hydrochloride | | 455 |
| 55 | 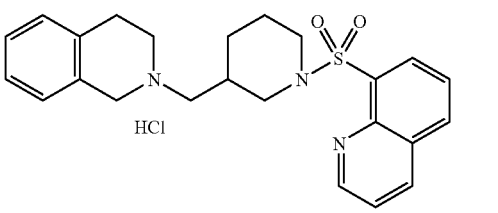 | 8-[4-(3,4-Dihydro-1H-isoquinolin-2-yl-methyl)-piperidine-1-sulfonyl]-quinoline hydrochloride | | 422 |
| 56 | 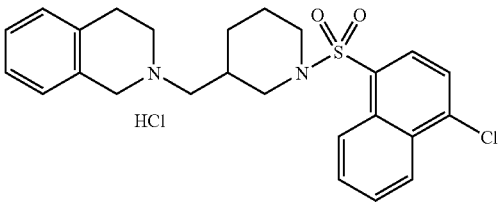 | 2-[1-(4-Chloro-naphtalene-1-sulfonyl)-piperidin-3-ylmethyl]-1,2,3,4-tetrahydro-isoquinoline hydrochloride | | 455 |
| 57 | 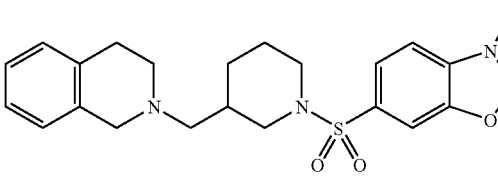 | 6-[3-(3,4-Dihydro-1H-isoquinolin-2-yl-methyl)-piperidine-1-sulfonyl]-3-methyl-3H-benzooxazol-2-one hydrochloride | | 442 |
| 58 | 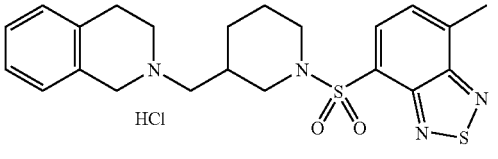 | 2-[1-(7-Methyl-benzo[1,2,5]-thiadiazole-4-sulfonyl)-piperidin-3-ylmethyl]-1,2,3,4-tetrahydroisoquinoline hydrochloride | | 443 |
| 59 | 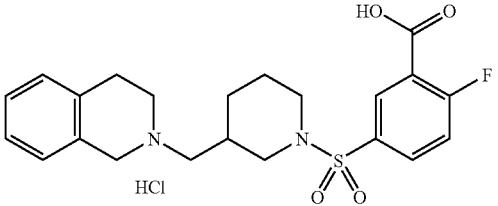 | 5-[3-(3,4-Dihydro-1H-isoquinolin-2-yl-methyl)-piperidine-1-sulfonyl]-2-fluoro-benzoic acid hydrochloride | | 433 |
| 60 | 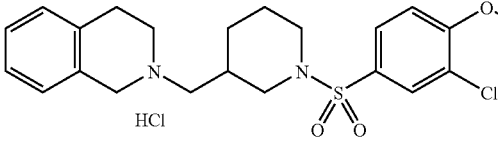 | 2-[1-(3Chloro-4-methoxy-benzene-sulfonyl)-piperidin-3-ylmethyl]-1,2,3,4-tetrahydro-isoquinoline hydrochloride | | 435 |
| 61 | 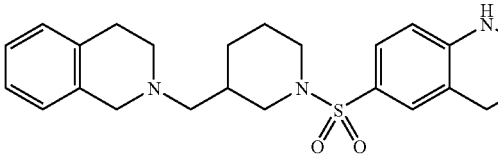 | 6-[3-(3,4-Dihydro-1H-isoquinolin-2-yl-methyl)-piperidine-1-sulfonyl]-3,4-dihydro-1H-quinolin-2-one | | 440 |

-continued

| No | STRUCTURE | Autonom | ¹H-NMR | MS (APCI) (M + H)⁺ |
|---|---|---|---|---|
| 62 | 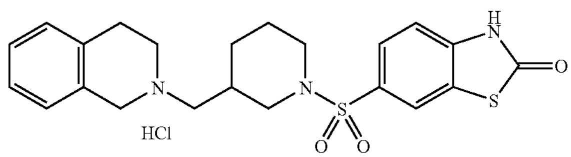 | 6-[3-(3,4-Dihydro-1H-isoquinolin-2-yl-methyl)-piperidine-1-sulfonyl]-3H-benzothiazol-2-one hydrochloride | | 444 |
| 63 | 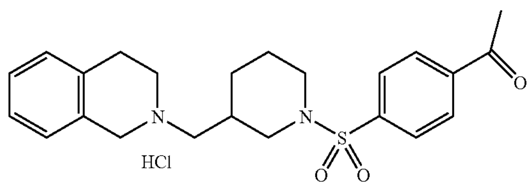 | 1{4-[3-(3,4-Dihydro-1H-isoquinolin-2-ylmethyl)-piperidine-1-sulfonyl]-phenyl}-ethanone hydrochloride | | 413 |
| 64 | 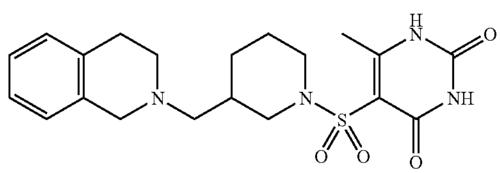 | 5-[3-(3,4-Dihydro-1H-isoquinolin-2-yl-methyl)-piperidine-1-sulfonyl]-6-methyl-1H-pyrimidine-2,4-dione | | 419 |
| 65 | 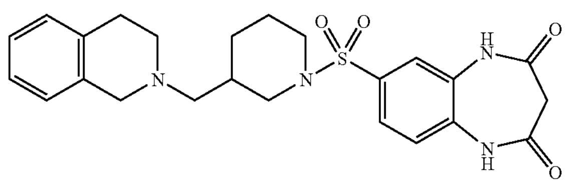 | 7-[3-(3,4-Dihydro-1H-isoquinolin-2-yl-methyl)-piperidine-1-sulfonyl]-1,5-dihydrobenzo[b][1,4]diazepine-2-dione | | 469 |
| 66 | 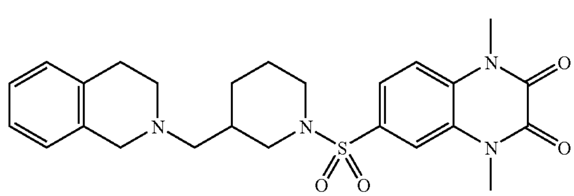 | 6-[3-(3,4-Dihydro-1H-isoquinolin-2-yl-methyl)-piperidine-1-sulfonyl]-1,4-dimethyl-1,4-dihydroquinoxaline-2,3-dione | | 483 |
| 67 | 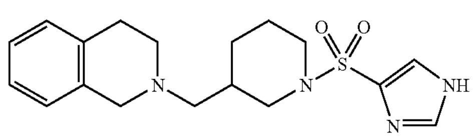 | 2-[1-(1H-Imidazole-4-sulfonyl)-piperidin-3-ylmethyl]-1,2,3,4-tetrahydro-isoquinoline | | 361 |
| 68 | 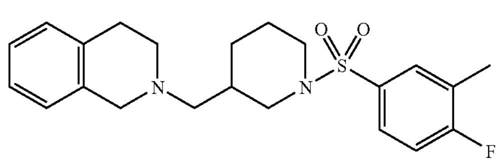 | 2-[1-(4-Fluoro-3-methyl-benzene-sulfonyl)-piperidin-3-ylmethyl]-1,2,3,4-tetrahydro-isoquinoline | | 403 |
| 69 | 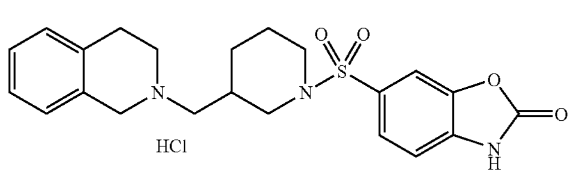 | 6-[3-(3,4-Dihydro-1H-isoquinolin-2-yl-methyl)-piperidine-1-sulfonyl]-3H-benzooxazol-2-one hydrochloride | | 428 |

-continued

| No | STRUCTURE | Autonom | ¹H-NMR | MS (APCI (M + H)⁺) |
|---|---|---|---|---|
| 70 | 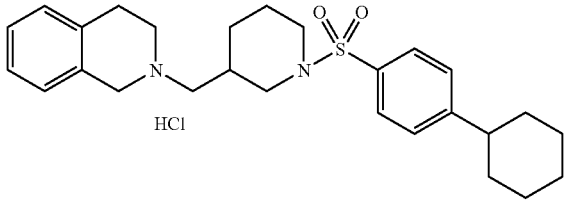 | 2-[1-(4-Cyclohexyl-benzenesulfonyl)-piperidin-3-ylmethyl]-1,2,3,4-tetrahydro-isoquinoline hydrochloride | | 453 |
| 71 | 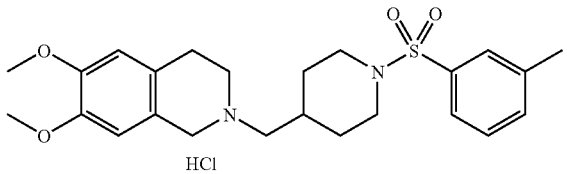 | 6,7-Dimethoxy-2-[1-(toluene-3-sulfonyl)-piperidin-4-ylmethyl]-1,2,3,4-tetrahydro-isoquinoline hydrochloride | | 481 |
| 72 | 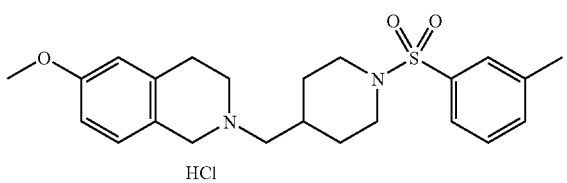 | 6-Methoxy-2-[1(toluene-3-sulfonyl)-piperidin-4-ylmethyl]-1,2,3,4-tetra-hydroiso-quinoline hydrochloride | | 415 |
| 73 | 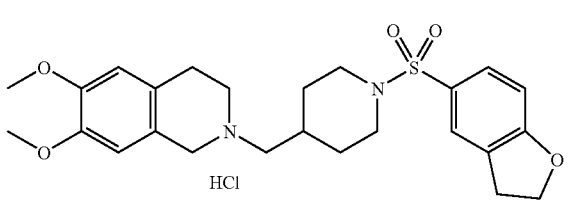 | 2-[1-(2,3-Dihydro-benzofuran-5-sulfonyl)-piperidin-4-ylmethyl]-6,7-dimethoxy-1,2,3,4-tetrahydroisoquinoline hydrochloride | | 473 |
| 74 | 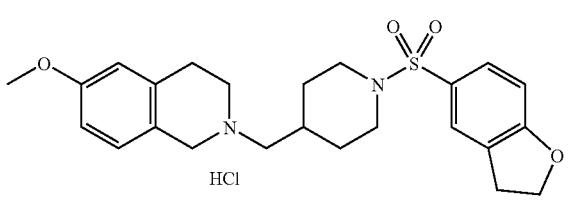 | 2-[1-(2,3-Dihydro-benzofuran-5-sulfonyl)-piperidin-4-ylmethyl]-6-methoxy-1,2,3,4-tetrahydroiso-quinoline hydrochloride | | 443 |
| 75 | 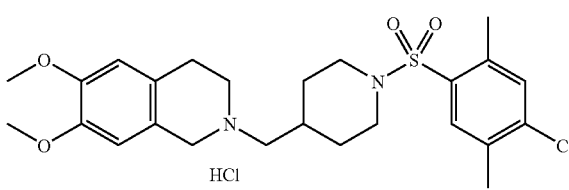 | 2-[1-(4-Chloro-2,5-dimethylbenzene-sulfonyl)-piperidin-4-ylmethyl]-6,7-dimethoxy-1,2,3,4-tetrahydroisoquinoline hydrochloride | | 493 |
| 76 | 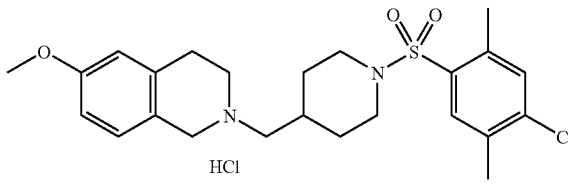 | 2-[1-(4-Chloro-2,5-dimethyl-benzene sulfonyl)-piperidin-4-ylmethyl]-6-methoxy-1,2,3,4-tetrahydro-isoquinoline hydrochloride | | 463 |
| 77 | 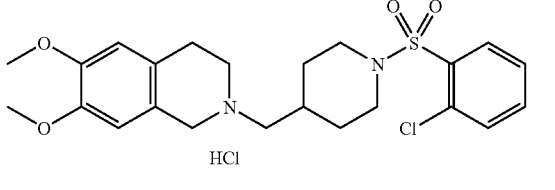 | 2-[1-(2-Chloro-benzene-sulfonyl)-piperidin-4-ylmethyl]-6,7-dimethoxy-tetrahydroisoquinoline hydrochloride | | 465 |

-continued

| No | STRUCTURE | Autonom | ¹H-NMR | MS (APCI) (M + H)⁺ |
|---|---|---|---|---|
| 78 | 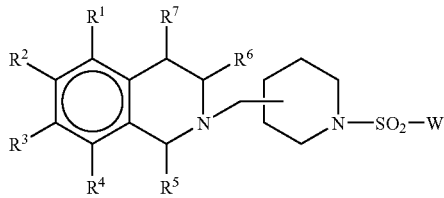 HCl | 2-[1-(2-Chloro-benzene-sulfonyl)-piperidin-4-ylmethyl]-6-methoxy-1,2,3,4-tetrahydro-isoquinoline hydrochloride | | 435 |

Biological Assays

Radioligand Binding

Radioligand binding assays were performed using the Cloned Human Serotonin Receptor, Subtype 7 (h5HT$_7$), expressed in CHO cells, coated on Flashplate (Basic Flash-Plate Cat.: SMP200) from PerkinElmer (Cat.: 6120512). The protocol assay was essentially the recommended protocol in the Technical Data Sheet by PerkinEmer Life and Analytical Sciences. The Mass membrane protein/well was typically 12 μg and the Receptor/well was about 9-10 fmoles. The Flashplate were let equilibrate at room temperature for one hour before the addition of the components of the assay mixture. The binding buffer was: 50 mM Tris-HCl, pH 7.4, containing 10 mM MgCl$_2$, 0.5 mM EDTA and 0.5% BSA. The radioligand was [$^{125}$I]LSD at a final concentration of 0.82 nM. Nonspecific binding was determined with 50 μM of Clozapine. The assay volume was 25 μl. TopSeal-A were applied onto Flashplate microplates and they were incubated at room temperature for 240 minutes in darkness. The radioactivity were quantified by liquid scintillation spectrophotometry (Wallac 1450 Microbeta Trilux) with a count delay of 4 minutes prior to counting and a counting time of 30 seconds per well. Competition binding data were analyzed by using the LIGAND program (Munson and Rodbard, LIGAND: A versatile, computerized approach for characterization of ligand-binding systems. *Anal. Biochem.* 107: 220-239, 1980) and assays were performed in triplicate determinations for each point. Results for representative compounds are given in the table 2 below:

TABLE 2

| COMPOUND | 5-HT7 IC-50 (nM) |
|---|---|
| 1 | 70.2 |
| 2 | 28.4 ± 18.2 |
| 3 | 76.4 |
| 5 | 63 |
| 6 | 18.2 ± 3.7 |
| 16 | 36.1 ± 16.0 |
| 22 | 16.8 ± 8.0 |
| 23 | 83.4 |

The invention claimed is:

1. A compound of the formula I:

(I)

wherein
  W is a substituted or unsubstituted alkyl, substituted or unsubstituted alkenyl, substituted or unsubstituted cycloalkyl, substituted or unsubstituted aryl, substituted or unsubstituted heterocyclyl;
  $R^1$, $R^2$, $R^3$, $R^4$, $R^5$, $R^6$ and $R^7$ are each independently selected from the group formed by hydrogen, substituted or unsubstituted alkyl, substituted or unsubstituted cycloalkyl, substituted or unsubstituted alkenyl, substituted or unsubstituted aryl, substituted or unsubstituted heterocyclyl, —COR$^8$, —C(O)OR$^8$, —C(O)NR$^8$R$^9$, —HC=NR$^8$, —CN, —OR$^8$, —OC(O)R$^8$, —S(O)$_t$—R$^8$, —NR$^8$R$^9$, —NR$^8$C(O)R$^9$, —NO$_2$, —N=CR$^8$R$^9$ or halogen; wherein
  t is 1, 2 or 3;
  $R^8$ and $R^9$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, halogen;
  and the 1,2,3,4-tetrahydroisoquinoline group is linked through the methylene group to positions 3 or 4 of the piperidine ring;
  or a pharmaceutically acceptable salt, isomer, prodrug or solvate thereof.

2. A compound according to claim 1 characterized in that 1,2,3,4-tetrahydroisoquinoline group is linked through metilene to position 4 of the piperidine ring.

3. A compound according to claim 1 characterized in that W is an aromatic group selected from substituted or unsubstituted aryl, substituted or unsubstituted heterocyclyl, or substituted or unsubstituted phenyl.

4. A compound according to claim 3 characterized in that W is selected from alkyl, alkoxy and/or halo substituted phenyl.

5. A compound according to claim 1 characterized in that $R^5$, $R^6$ and $R^7$ are H.

6. A compound according to claim 1 characterized in that $R^1$ and $R^4$ are H.

7. A compound according to claims 5 or 6 wherein $R^2$ is alkoxy, and $R^3$ is H or alkoxy.

8. A process for the preparation of a compound of formula (I) or a salt, isomer or solvate thereof as claimed in any of claims 1-7, which comprises coupling of compounds of Formula (IIa) or (IIb):

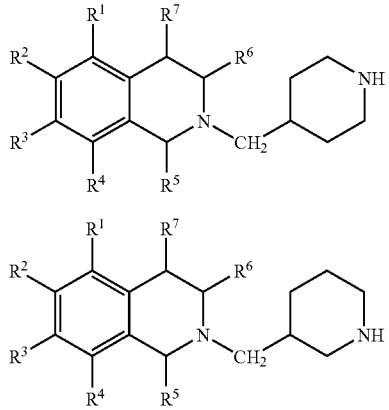

in which $R^1$-$R^7$ are as defined in Formula (I), with a compound of Formula (III):

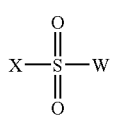

in which W is as defined in Formula (I) and X is an halogen, preferably Cl.

9. A pharmaceutical composition which comprises a compound as defined in any of claims 1-7 or a pharmaceutically acceptable salt, prodrug, isomer or solvate thereof, and a pharmaceutically acceptable carrier, adjuvant or vehicle.

10. A pharmaceutical composition according to claim 9 for oral administration.

11. A method of manufacturing a medicament comprising combining a compound as defined in any of claims 1-7 with a pharmaceutically acceptable carrier.

12. A compound according to claim 2 characterized in that W is an aromatic group selected from substituted or unsubstituted aryl, substituted or unsubstituted heterocyclyl, or substituted or unsubstituted phenyl.

13. A compound according to claim 12 characterized in that W is selected from alkyl, alkoxy and/or halo substituted phenyl.

14. A compound according to claim 2 characterized in that $R^5$, $R^6$ and $R^7$ are H.

15. A compound according to claim 3 characterized in that $R^5$, $R^6$ and $R^7$ are H.

16. A compound according to claim 4 characterized in that $R^5$, $R^6$ and $R^7$ are H.

17. A compound according to claim 12 characterized in that $R^5$, $R^6$ and $R^7$ are H.

18. A compound according to claim 13 characterized in that $R^5$, $R^6$ and $R^7$ are H.

19. A compound according to claim 2 characterized in that $R^1$ and $R^4$ are H.

20. A compound according to claim 3 characterized in that $R^1$ and $R^4$ are H.

21. A compound according to claim 4 characterized in that $R^1$ and $R^4$ are H.

22. A compound according to claim 5 characterized in that $R^1$ and $R^4$ are H.

23. A compound according to claim 12 characterized in that $R^1$ and $R^4$ are H.

24. A compound according to claim 13 characterized in that $R^1$ and $R^4$ are H.

25. A compound according to claim 14 characterized in that $R^1$ and $R^4$ are H.

26. A compound according to claim 15 characterized in that $R^1$ and $R^4$ are H.

27. A compound according to claim 16 characterized in that $R^1$ and $R^4$ are H.

28. A compound according to claim 17 characterized in that $R^1$ and $R^4$ are H.

29. A compound according to claim 18 characterized in that $R^1$ and $R^4$ are H.

30. A compound according to claim 5 wherein $R^2$ is methoxy, and $R^3$ is H or methoxy.

31. A compound according to claim 6 wherein $R^2$ is methoxy, and $R^3$ is H or methoxy.

* * * * *